United States Patent
Valk et al.

(10) Patent No.: US 11,357,425 B2
(45) Date of Patent: Jun. 14, 2022

(54) INTRAOSSEOUS IMPLANTED BIOLOGICAL SENSOR

(71) Applicant: ADMETSYS CORPORATION, Boston, MA (US)

(72) Inventors: Jeffrey Valk, Boston, MA (US); Timothy Valk, Boston, MA (US)

(73) Assignee: ADMETSYS CORPORATION, Boston, MA (US)

( * ) Notice: Subject to any disclaimer, the term of this patent is extended or adjusted under 35 U.S.C. 154(b) by 0 days.

(21) Appl. No.: 16/976,104

(22) PCT Filed: Mar. 11, 2019

(86) PCT No.: PCT/US2019/021559
§ 371 (c)(1),
(2) Date: Aug. 27, 2020

(87) PCT Pub. No.: WO2019/177938
PCT Pub. Date: Sep. 19, 2019

(65) Prior Publication Data
US 2021/0038130 A1 Feb. 11, 2021

Related U.S. Application Data

(60) Provisional application No. 62/641,737, filed on Mar. 12, 2018.

(51) Int. Cl.
*A61B 5/145* (2006.01)
*A61B 5/00* (2006.01)

(52) U.S. Cl.
CPC ........ *A61B 5/14503* (2013.01); *A61B 5/0004* (2013.01); *A61B 5/4839* (2013.01); *A61B 5/6878* (2013.01); *A61B 5/742* (2013.01)

(58) Field of Classification Search
CPC ............. A61B 5/1455; A61B 5/14551; A61B 5/14532; A61B 5/1459; A61B 5/14503;
(Continued)

(56) References Cited

U.S. PATENT DOCUMENTS

| 8,080,003 B1* | 12/2011 | Burton | A61B 5/6878 |
| | | | 604/891.1 |
| 9,974,483 B2* | 5/2018 | Hyun | A61B 5/150839 |

(Continued)

FOREIGN PATENT DOCUMENTS

CA 2458966 C 2/2013

OTHER PUBLICATIONS

International Search Report and Written Opinion dated May 28, 2019, in related PCT application No. PCT/US2019/021559, 8 pages.

*Primary Examiner* — Chu Chuan Liu
(74) *Attorney, Agent, or Firm* — Fox Rothschild LLP

(57) ABSTRACT

A method and system for monitoring analytes in the circulatory system of an individual is provided. A biological sensor is implanted in the bone marrow of a patient and may be self contained within a housing. The biological sensor measures physiological parameters of a patient, including analytes, on a fixed or adjustable schedule. The biological sensor includes a control unit having a transmitter and an energy source for providing energy to the control unit. The biological sensor may be used to adjust other medical treatments and devices in a closed or semi closed loop mechanism and/or predict patient treatment.

11 Claims, 2 Drawing Sheets

(58) Field of Classification Search
CPC ..... A61B 5/4839; A61B 5/6878; A61B 5/742; A61B 5/0004; A61B 5/4845
See application file for complete search history.

(56) References Cited

U.S. PATENT DOCUMENTS

| | | |
|---|---|---|
| 2010/0145317 A1 | 6/2010 | Laster et al. |
| 2010/0191088 A1 | 7/2010 | Anderson et al. |
| 2010/0261983 A1 | 10/2010 | Scarantino et al. |
| 2016/0212783 A1* | 7/2016 | Hampapuram ........ G16H 40/63 |
| 2016/0331284 A1* | 11/2016 | Pace .................. A61B 5/14532 |

* cited by examiner

INTRAOSSEOUS IMPLANTED BIOLOGICAL SENSOR

FIELD OF THE INVENTION

The invention relates to the field of biological sensors. More particularly, the invention relates to an intraosseous implantable biological sensor.

BACKGROUND OF THE INVENTION

Biological sensors are known. However, what is needed is a biological sensor that can be implanted into the bone marrow for long-term to assaying of circulating active and inactive substances which relate to physiologic and pathologic processes.

BRIEF SUMMARY OF THE INVENTION

The foregoing need is addresses by the intraosseous implantable biological sensor in accordance with the invention.

The method and system in accordance with the invention monitors analytes in the circulation by providing a biological sensor that is embedded in the bone marrow of a patient and may be self contained within a housing. The functional system is entirely embedded within a patient's body. The biological sensor may measure physiological parameters of a patient, including analytes, on a fixed or adjustable schedule.

The biological sensor includes a control unit having a transmitter and an energy source for providing energy to the control unit. The biological sensor may be used to adjust other medical treatments and devices in a closed or semi closed loop mechanism or predict patient treatment.

The biological sensor includes a membrane that can be used to access component in the biological sensor to replace or replenish them a system by use of a temporary external attachment using a catheter or other delivery device. The biological sensor may be easily removed from the implantatione site and its component parts removed and/or replaced in whole or in part.

The housing of the biological sensor may be coated with a biocompatible or inert material or may comprise a biocompatible or inert material.

The biological sensor may also include an integrated treatment system providing treatment to a patient based on the data received from the sensing units. Alternatively, the treatment system may be implanted in another surgical site or may be external to the patient but connectable to the patient by catheters, tubing and the isle for delivery of medications. The treatment may be initiated by the control unit immediately upon receiving data from the sensing units or may be varied over time based on data received from the sensing units. Alternatively, treatment may be suggested, i.e. on the display of an external computing system, but not activated.

The biological sensor may also include an embedded energy source and control unit including a transmitter. Alternatively, the energy source and/or transmitter are separate from the biological sensor.

The control unit may be integrated into the biological sensor or may be external to the biological sensor positioned in another part of the body or alternatively external to the body. The control unit may adjust the parameters of system and monitor settings by use of wireless command.

The sensor for measuring analytes in accordance with the invention includes a housing having an interior; a housing control unit positioned within the housing and having a transmitter and a receiver; an energy source positioned within the housing for providing energy to the control unit; one or more sensing units disposed at least partially within the housing and extending from the housing into a bone marrow of a patient, and a membrane covering a part of the housing that is configured to allow access to the interior of the housing.

The sensor further includes an ancillary control unit located remotely from the sensor and in communication with the housing control unit. The ancillary control unit has a display for displaying information received from the sensing units through the housing control unit.

The housing control unit may receives a signal from the one or more sensing units and transmits to the ancillary control unit. The ancillary control unit includes a display and the signal includes patient analyte data that may be displayed on the display.

The housing control unit is configured to receive a signal from the at least one or more sensing units, the signal including patient analyte data and may transmit instructions to the at least one or more sensing units to measure analytes data on a fixed or adjustable schedule. Alternatively, the housing control unit may receive a signal from the at least one or more sensing units and transmit it to the ancillary control unit and the ancillary control unit transmits instructions to the one or more sensing units to adjust the measurement of analytes. The ancillary control unit or the housing control unit may also transmit instructions to a treatment system to deliver medications to the patient based on the patient analyte data contained within the signal. The treatment system may be housed within the housing or located remotely from a site where the sensor is implanted.

The one or more sensing units may be removable and replaceable and/or capable of being restored or reconditioned through the housing membrane.

The sensor includes a replaceable or renewable energy source selected from one or more replaceable batteries or a self generating system which uses a process such as motion or vascular flow, body heat, or chemical reaction.

These and other aspects of the biological sensor will be further described herein.

BRIEF DESCRIPTION OF THE DRAWINGS

For a better understanding of the invention, and to show how the same may be carried into effect, reference will now be made, by way of example, to the accompanying drawings, in which.

DETAILED DESCRIPTION OF THE INVENTION

Figure 1:
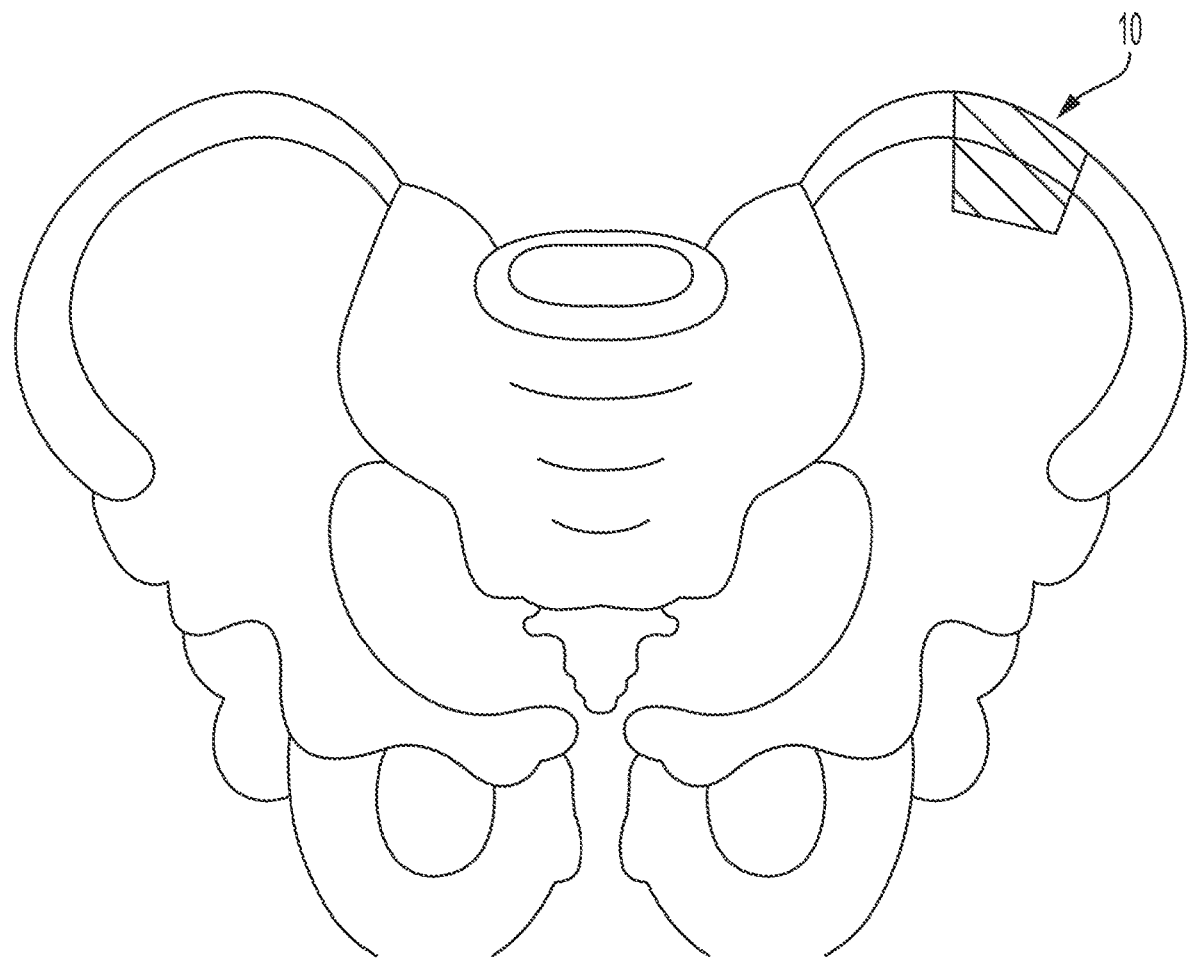
FIG. 1 is an illustration depicting a pelvis identifying a location site for implanting the sensor in accordance with the invention.
Figure 2:
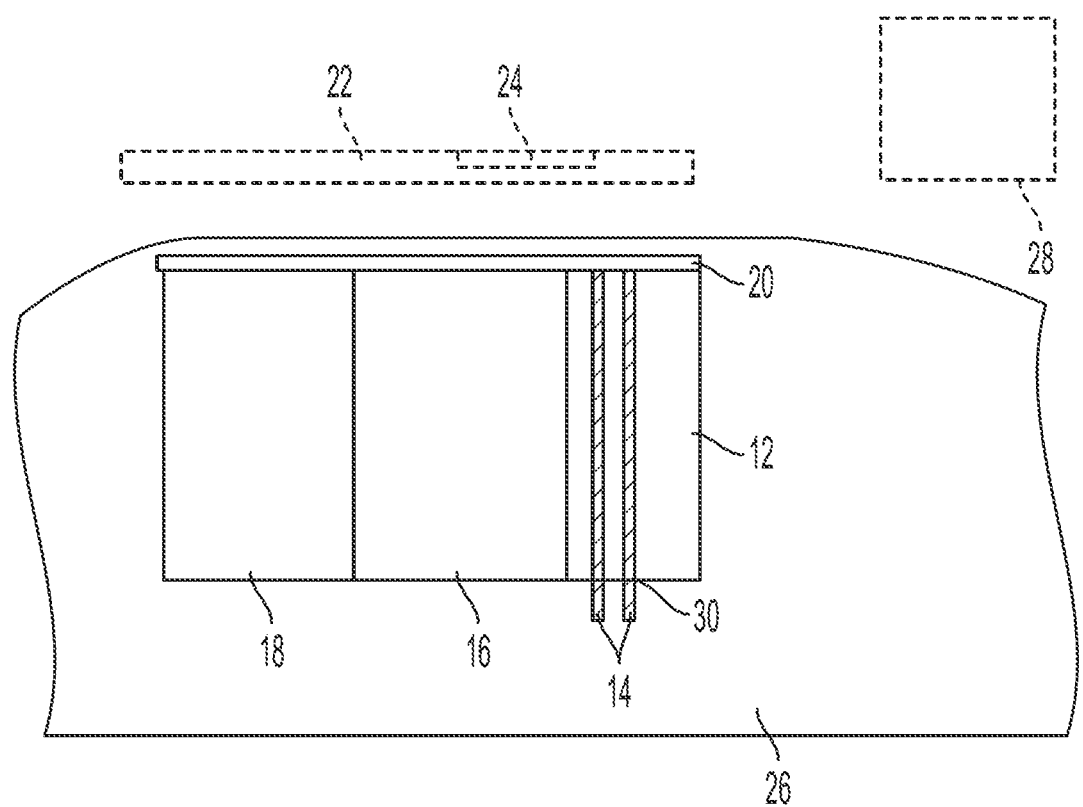
FIG. 2 is a schematic diagram of the sensor in accordance with the invention.

Referring to FIGS. 1 and 2 the intraosseous implantable biological sensor in accordance with the invention will now be described. The sensor 10 broadly includes a housing 12, one or more sensing units 14, a control unit 16 and an energy source 18. The housing 12 includes a membrane 20 thereon that allows replacement and/or replenishment of individual parts, such as sensing units 14. An ancillary processing device can also be utilized and may integrated into the sensor or positioned and used at a remote location.

Sensor 10 may direct automated and semi automated treatment techniques such as closed, and partially closed loop infusions. The insertion into the marrow space allows measurement through small blood channels while allowing the sensor 10 to be fixed directly to tissue. In addition, the sensor 10 is embedded (implanted) so that the skin and subcutaneous tissues cover it allowing minimal external compromise.

Sensing units 14 may include optical, enzymatic, calorimetry, thermal, spectroscopy, or "lab on a chip." These may be in a combined modality and other non specified technologies may also be used. The device may measure one or more analytes over various time cycles. These may be fixed or controlled externally by a wireless method to adjust the timing of the sensor 10.

Control unit 16 may include a receiver for receiving a signal from the sensing units that includes physiological data of the patient. The control unit 16 may also includes a transmitter that may transmit the signal to a remotely located ancillary processing device 22 for analysis. The processing device 22 may include a display screen for displaying the analyzed data to monitor the condition of the patient. Data generated from the sensing units 14 may alter treatment settings of respirators, dialysis systems, pacemakers, defibrillators and intravenous, intraarterial, interstitial, cerebrospinal and subcutaneous injections and infusions as well as alteration and adjustment of other medical devices or treatments. Control unit 16 may include memory having a data base of knowledge including known normative data related to interpreting the analyte data received from the sensing units. Control unit 16 receives a signal from the sensing units which contains patient physiological parameters and analyzes the physiological parameters and other data obtained from the sensing units 14. Control unit 16 analyzes the data (i) in isolation as it is received; (ii) in the context of measurement and analysis based on the past history of the patient, which is stored in memory; or (iii) cross-references the patient data in the signal and cross-references it with the known normative data in the database. Alternatively, control unit 16 transmit the signal to a remotely located ancillary processing/control unit 22. The processing unit 22 optionally includes a display device 24 for displaying the output. The control unit 16 or the ancillary processing unit 22 can also include information related to goal-directed therapies associated with particular disease states for providing suggested goal-directed treatments based on the cross-referencing step and outputs a suggested treatment by transmitting it wirelessly or by wire to a treatment system 28. The treatment system 28 may include one or more medications for delivering the medications to a patient.

In addition the sensing units 14 could monitor potentially toxic substances such as inhalants or injurious materials allowing rapid treatment, for example antidotes Such treatment could be integrated with a separate embedded structure and could be initialed by a signal from the sensor. This treatment component could be embedded in the marrow 26 or another part of the body.

Energy source 18 may include one or more replaceable batteries or a self generating system which uses a process such as motion or vascular flow, body heat, or chemical reaction. These in combination with other sources known to those of skill in the art may also be used.

The sensor is configured to measure and record numerous analytes including but not limited to biochemical, hormonal, inflammatory, hematologic, genetic/nucleic acid and physiologic concentrations, vascular pressures, flow rates, pharmacologic concentrations, degradation products, pH, oxygen, carbon dioxide, toxic exposures, metabolic factors such as glucose, lactate, electrolytes; hormones such as cortisol, insulin, epinephrine; drug and drug metabolites; other therapeutic substances such as monoclonal antibodies, ligands, and chemotherapeutic agents; hematologically active substances such coagulants and anticoagulants; DNA, RNA and nucleic acid containing substances.

The sensor 10 may be implanted by surgical insertion and remain without extension through the skin. The area of implantation is pelvic and usually the ileum but not restricted to these sites. The housing 12 may comprise biologically inert or biocompatible material such as polymers, stainless steel, silicone and the like. The housing membrane 20 is porous so as to allow contact with the marrow circulation without producing inflammation and/or rejection. Regeneration of the sensing units 14 could be through injection or insertion of new material through temporary use of a catheter or needle into the device or alternatively extraction of the sensing units and replacement such as in a self contained form. Those of skill in the art will also appreciate that although long-term use is contemplated the entire sensor may be replaced or individual parts such as the energy source 18 or control unit 16 may be replaced or replenished.

While the invention has been described with reference to the specific embodiments thereof, those skilled in the art will be able to make various modifications to the described embodiments of the invention without departing from the true spirit and scope of the invention. The terms and descriptions used herein are set forth by way of illustration only and are not meant as limitations. Those skilled in the art will recognize that these and other variations are possible within the spirit and scope of the invention as defined in the following claims and their equivalents.

What is claimed:

1. A sensor system for measuring one or more analytes in a subject, the sensor system comprising:
   an implantable sensor device configured for implantation into a bone marrow region of the subject, the implantable sensor device comprising:
   a housing having an interior;
   a housing control unit positioned within the housing, the control unit comprising a transmitter and a receiver;
   an energy source positioned within the housing for providing energy to the housing control unit, the energy source comprising a self-generating system that is configured to use at least one of the following processes for generation of energy: motion flow, vascular flow, body heat, or chemical reaction;
   one or more sensing units included within the housing, the sensing units in communication with the housing control unit;
   a porous membrane covering at least a part of the housing, the porous membrane being configured to allow analytes from outside the housing to enter the interior of the housing and contact the one or more sensing units,
   wherein the sensor system is configured for collection and analysis of analyte data corresponding to the bone marrow region of the subject upon implantation.

2. The sensor system of claim 1, further comprising a remote control unit located remotely from the implantable sensor device, and in communication with the housing control unit, the remote control unit having a display.

3. The sensor system of claim 2, wherein the housing control unit is configured to:

receive, from at least one of the one or more sensing units, analyte data corresponding to the bone marrow of the subject; and transmit the received analyte data to the remote control unit.

4. The sensor system of claim 3, wherein the remote control unit is configured to display the analyte data on the display.

5. The sensor system of claim 1, wherein the housing control unit is configured to:

receive a signal from at least one of the one or more sensing units, said signal including analyte data corresponding to the bone marrow region of the subject; and transmit instructions to said at least one of the one or more sensing units to measure analytes data on a fixed or adjustable schedule.

6. The sensor system of claim 1, wherein the one or more sensing units are removable and replaceable.

7. The sensor system of claim 1, further comprising a treatment system configured for providing medication to the subject, the treatment system housed within the housing of the implantable sensor device or located remotely from the implantable sensor device.

8. The sensor system of claim 7, wherein the housing control unit is configured to:

receive a signal from at least one of the one or more sensing units, said signal including analyte data corresponding to the bone marrow region of the subject;

identify, based on the analyte data, a treatment plan for the subject; and transmit instructions to the treatment system to deliver medication to the subject in accordance with the treatment plan.

9. The sensor system of claim 1, wherein the energy source comprises one or more replaceable batteries.

10. The sensor system of claim 1, wherein the analytes comprise at least one of the following: biochemical analytes, hormonal analytes, inflammatory analytes, hematologic analytes, genetic/nucleic acid analytes, physiologic analytes, vascular pressures related analytes, flow rates-related analytes, pharmacologic concentration related analytes, degradation products, pH related analytes, oxygen, carbon dioxide, toxic exposure related analytes, metabolic factor-related analytes, glucose, lactate, electrolytes, hormones related analytes, cortisol, insulin, epinephrine, drug related analytes, drug metabolites; monoclonal antibodies, ligands, chemotherapeutic agents, hematologically active substances, coagulants, anticoagulants, DNA, RNA, or nucleic acid containing substances.

11. The sensor system of claim 1, wherein the implantable sensor device is implantable in a pelvic region of a patient.

* * * * *